(12) United States Patent
Lundquist et al.

(10) Patent No.: US 7,838,847 B2
(45) Date of Patent: Nov. 23, 2010

(54) SUBSTRATES, SYSTEMS AND METHODS FOR ANALYZING MATERIALS

(75) Inventors: Paul Lundquist, San Jose, CA (US); Stephen Turner, Menlo Park, CA (US)

(73) Assignee: Pacific Biosciences of California, Inc., Menlo Park, CA (US)

(*) Notice: Subject to any disclaimer, the term of this patent is extended or adjusted under 35 U.S.C. 154(b) by 0 days.

(21) Appl. No.: 11/981,796

(22) Filed: Oct. 31, 2007

(65) Prior Publication Data

US 2008/0152280 A1    Jun. 26, 2008

Related U.S. Application Data

(63) Continuation of application No. 11/849,157, filed on Aug. 31, 2007.

(60) Provisional application No. 60/841,897, filed on Sep. 1, 2006.

(51) Int. Cl.
*G01N 21/64* (2006.01)
(52) U.S. Cl. .................................. 250/458.1
(58) Field of Classification Search ............... 250/458.1
See application file for complete search history.

(56) References Cited

U.S. PATENT DOCUMENTS

| | | | |
|---|---|---|---|
| 5,094,517 A | 3/1992 | Franke | |
| 5,157,262 A | 10/1992 | Marsoner et al. | |
| 5,173,747 A | 12/1992 | Boiarski et al. | |
| 5,192,502 A | 3/1993 | Attridge et al. | |
| 5,233,673 A | 8/1993 | Vali et al. | |
| 5,239,178 A | 8/1993 | Derndinger et al. | |
| 5,439,647 A | 8/1995 | Saini | |
| 5,446,534 A | 8/1995 | Goldman | |
| 5,470,710 A | 11/1995 | Weiss et al. | |
| 5,545,531 A | 8/1996 | Rava et al. | |
| 5,547,839 A | 8/1996 | Dower et al. | |
| 5,578,832 A | 11/1996 | Trulson et al. | |
| 5,631,734 A | 5/1997 | Stern et al. | |
| 5,677,196 A * | 10/1997 | Herron et al. | ............ 436/518 |
| 5,695,934 A | 12/1997 | Brenner | |

(Continued)

FOREIGN PATENT DOCUMENTS

EP    1105529 B1    11/2005

(Continued)

OTHER PUBLICATIONS

Bernini et al., "Polymer-on-glass waveguide structure for efficient fluorescence-based optical biosensors," 2005, Proceedings of SPIE, vol. 5728, pp. 101-111.*

(Continued)

*Primary Examiner*—David P Porta
*Assistant Examiner*—Kiho Kim
(74) *Attorney, Agent, or Firm*—Deana A. Arnold

(57) ABSTRACT

Substrates, systems and methods for analyzing materials that include waveguide arrays disposed upon or within the substrate such that evanescent fields emanating from the waveguides illuminate materials disposed upon or proximal to the surface of the substrate, permitting analysis of such materials. The substrates, systems and methods are used in a variety of analytical operations, including, inter alia, nucleic acid analysis, including hybridization and sequencing analyses, cellular analyses and other molecular analyses.

19 Claims, 9 Drawing Sheets

U.S. PATENT DOCUMENTS

| | | | |
|---|---|---|---|
| 5,744,305 | A | 4/1998 | Fodor et al. |
| 5,812,709 | A | 9/1998 | Arai et al. |
| 5,821,058 | A | 10/1998 | Smith et al. |
| 5,867,266 | A | 2/1999 | Craighead et al. |
| 6,071,748 | A | 6/2000 | Modlin et al. |
| 6,192,168 | B1* | 2/2001 | Feldstein et al. ............... 385/12 |
| 6,210,896 | B1 | 4/2001 | Chan |
| 6,236,945 | B1 | 5/2001 | Simpson et al. |
| 6,263,286 | B1 | 7/2001 | Gilmanshin et al. |
| 6,388,788 | B1 | 5/2002 | Harris et al. |
| 6,437,345 | B1* | 8/2002 | Bruno-Raimondi et al. ............... 250/458.1 |
| 6,438,279 | B1 | 8/2002 | Craighead et al. |
| 6,603,537 | B1 | 8/2003 | Dietz et al. |
| 6,690,002 | B2 | 2/2004 | Kuroda et al. |
| 6,699,655 | B2 | 3/2004 | Nikiforov |
| 6,784,982 | B1 | 8/2004 | Blumenfeld et al. |
| 6,800,860 | B2 | 10/2004 | Dietz et al. |
| 6,818,395 | B1 | 11/2004 | Quake et al. |
| 6,867,851 | B2 | 3/2005 | Blumenfeld et al. |
| 6,869,764 | B2 | 3/2005 | Williams et al. |
| 6,917,726 | B2 | 7/2005 | Levene et al. |
| 6,919,211 | B1 | 7/2005 | Fodor et al. |
| 6,979,830 | B2 | 12/2005 | Dietz et al. |
| 6,982,146 | B1 | 1/2006 | Schneider et al. |
| 7,008,766 | B1 | 3/2006 | Densham |
| 7,033,762 | B2 | 4/2006 | Nelson et al. |
| 7,033,764 | B2 | 4/2006 | Korlach et al. |
| 7,052,847 | B2 | 5/2006 | Korlach et al. |
| 7,056,661 | B2 | 6/2006 | Korlach et al. |
| 7,056,676 | B2 | 6/2006 | Korlach et al. |
| 7,064,197 | B1 | 6/2006 | Rabbani et al. |
| 7,075,695 | B2 | 7/2006 | Gronbach |
| 7,081,954 | B2 | 7/2006 | Sandstrom |
| 7,083,914 | B2 | 8/2006 | Seul et al. |
| 7,130,041 | B2 | 10/2006 | Bouzid et al. |
| 7,135,667 | B2 | 11/2006 | Oldham et al. |
| 7,139,074 | B2 | 11/2006 | Reel |
| 7,145,645 | B2 | 12/2006 | Blumenfeld et al. |
| 7,189,361 | B2 | 3/2007 | Carson |
| 7,199,357 | B1 | 4/2007 | Oldham et al. |
| 7,209,836 | B1 | 4/2007 | Schermer et al. |
| 7,227,128 | B2 | 6/2007 | Sagatelyan |
| 7,233,393 | B2 | 6/2007 | Tomaney et al. |
| 7,292,742 | B2 | 11/2007 | Levene et al. |
| 7,302,348 | B2 | 11/2007 | Ghosh et al. |
| 7,323,681 | B1 | 1/2008 | Oldham et al. |
| 7,709,808 | B2 | 5/2010 | Reel et al. |
| 2002/0110839 | A1* | 8/2002 | Bach et al. ............... 435/7.9 |
| 2002/0113213 | A1* | 8/2002 | Amirkhanian et al. ... 250/458.1 |
| 2002/0146047 | A1* | 10/2002 | Bendett et al. ............... 372/40 |
| 2003/0044781 | A1 | 3/2003 | Korlach et al. |
| 2003/0077610 | A1 | 4/2003 | Nelson et al. |
| 2003/0138180 | A1* | 7/2003 | Kondo et al. ............... 385/3 |
| 2003/0174324 | A1 | 9/2003 | Sandstrom |
| 2003/0174992 | A1 | 9/2003 | Levene et al. |
| 2003/0186276 | A1 | 10/2003 | Odera |
| 2003/0190647 | A1 | 10/2003 | Odera |
| 2003/0194740 | A1 | 10/2003 | Williams |
| 2003/0215862 | A1 | 11/2003 | Parce et al. |
| 2004/0046128 | A1* | 3/2004 | Abel et al. ............... 250/458.1 |
| 2004/0048301 | A1 | 3/2004 | Sood et al. |
| 2004/0224319 | A1 | 11/2004 | Sood et al. |
| 2005/0135974 | A1 | 6/2005 | Harvey et al. |
| 2005/0175273 | A1 | 8/2005 | Iida et al. |
| 2005/0206895 | A1 | 9/2005 | Salmelainen |
| 2006/0103850 | A1* | 5/2006 | Alphonse et al. ............ 356/479 |
| 2007/0036511 | A1 | 2/2007 | Lundquist et al. |
| 2007/0048748 | A1 | 3/2007 | Williams et al. |
| 2007/0099212 | A1 | 5/2007 | Harris |
| 2007/0188746 | A1* | 8/2007 | Kraus et al. ................. 356/244 |
| 2007/0188750 | A1 | 8/2007 | Lundquist et al. |
| 2007/0206187 | A1 | 9/2007 | Lundquist et al. |
| 2008/0020938 | A1 | 1/2008 | Kaplan |
| 2008/0030628 | A1 | 2/2008 | Lundquist et al. |
| 2008/0128627 | A1 | 6/2008 | Lundquist et al. |

FOREIGN PATENT DOCUMENTS

| | | |
|---|---|---|
| WO | WO 91/06678 A1 | 5/1991 |
| WO | WO 96/27025 A1 | 9/1996 |
| WO | WO 99/05315 | 2/1999 |
| WO | WO 00/36152 A1 | 6/2000 |
| WO | WO 01/16375 A2 | 3/2001 |
| WO | WO 2004/100068 A2 | 11/2004 |
| WO | WO 2006/116726 A2 | 2/2006 |
| WO | WO 2006/135782 A2 | 12/2006 |
| WO | WO 2007/002367 A2 | 1/2007 |
| WO | WO 2007/011549 A1 | 1/2007 |
| WO | WO 2008/002765 A2 | 1/2008 |

OTHER PUBLICATIONS

Herron et al. "Orientation and Activity of Immobilized Antibodies," 2003, In: Biopolymers at Interfaces, 2nd Edition (M. Malmsten, Ed.), Surfactant Science Series, vol. 110, Marcel Dekker, New York, pp. 115-163.*

Weissman et al., "Mach-Zhnder type, evanescent-wave bio-sensor, in ion-exchnaged glass, using periodically segmented waveguide," 1999, Proceedings of SPIE, vol. 3596, pp. 210-216.*

Feldstein et al., "Array Biosensor: optical and fluidics systems," 1999, Journal of Biomedical Microdevices, vol. 1, pp. 139-153.*

M.J. Levene, et al. (Jan. 31, 2003) "Zero-mode Waveguides for Single-molecule Analysis at High Concentrations." Science, 299: 682-686.

Boiarski et al., "Integrated-optic sensor with macro-flow cell" Proc. SPIE (1992) 1793:199-211.

Budach et al., "Planar waveguides as high-performance sensing platforms for fluorescence-based multiplexed oligonucleotide hybridization assays" Anal. Chem. (1999) 71(16):3347-3355.

Cottier et al., "Thickness-modulated waveguides for integrated optical sensing" Proc. SPIE (2002) 4616:53-63.

Duveneck et al., "Planar waveguides for ultra-high sensitivity of the analysis of nucleic acids" Anal Chem Acta (2002) 469:49-61.

Salama et al., "Modeling and simulations of luminescence detection platforms" Biosensors & Bioelectronics (2004) 19:1377-1386.

Wu et al., "DNA and protein microarray printing on silicon nitride waveguide surfaces" Biosensors and Bioelectronics (2006) 21:1252-1263.

* cited by examiner

SUBSTRATES, SYSTEMS AND METHODS FOR ANALYZING MATERIALS

CROSS-REFERENCE TO RELATED APPLICATIONS

This application a continuation U.S. patent application Ser. No. 11/849,157 filed Aug. 31, 2007, which claims priority to Provisional U.S. Patent Application No. 60/841,897, filed Sep. 1, 2006, the full disclosure of which is incorporated herein by reference for all purposes.

STATEMENT REGARDING FEDERALLY SPONSORED RESEARCH

Not applicable.

BACKGROUND OF THE INVENTION

A large number of analytical operations benefit from the simultaneous illumination of relatively large area of substrates in order to accomplish the desired analysis. For example, interrogation of biopolymer array substrates typically employs wide area illumination, e.g., in a linearized beam, flood or reciprocating spot operation. Such illumination allows interrogation of larger numbers of analytical features, e.g., molecule groups, in order to analyze the interaction of such molecule groups with a sample applied to the array.

In the case of DNA arrays, in particular, large numbers of oligonucleotide probes are provided in discrete locations on a planar substrate surface, such that the surface comprises multiple, small patches of identical probes, where the probes' nucleotide sequence for each patch location is known. When one applies a labeled sample sequence to the array, the position on the array to which the sample hybridizes is indicative of the complementary probe sequence, and as such, the sequence of the sample sequence. These arrays are generally interrogated using laser based fluorescence microscopes that are capable of applying excitation illumination over large areas of the substrate in order to interrogate all of the patches. Such systems have employed galvo scanners, slower, scanning microscopes, linearized beam illumination, and wide area flood illumination.

In some cases, however, a more tightly controlled illumination strategy may be desired. For example, it may be desirable to provide stricter control of the volume of material that is illuminated, as well as the overall area that is illuminated, effectively controlling illumination not only in one of the x or y axes of a planar substrate, but also in the z axis, extending away from the substrate. One example of controlled illumination that accomplishes both lateral (x and y) and volume (z) control is the use of zero mode waveguides as a base substrate for analyzing materials. See, U.S. Pat. Nos. 6,991,726 and 7,013,054, the full disclosures of which are hereby incorporated herein by reference in their entirety for all purposes. Briefly, zero mode waveguide array substrates employ an opaque cladding layer, e.g., aluminum, chromium, or the like, deposited over a transparent substrate layer, and through which are disposed a series of apertures through to the transparent layer. Because the apertures are of sufficiently small cross sectional dimensions, e.g., on the order of 50-200 nm in cross section, they prevent propagation of light through them that is below a cut-off frequency. While some light will enter the aperture or core, its intensity decays exponentially as a function of the distance from the aperture's opening. As a result, a very small volume of the core is actually illuminated with a relevant level of light. Such ZMW arrays have been illuminated using a number of the methods described herein, including spot illumination, flood illumination and line illumination (using a linearized beam)(See, e.g., co-pending U.S. patent application Ser. Nos. 11/483,413 (filed Jul. 5, 2006), and 60/772,908 (filed Feb. 13, 2006), the full disclosures of which are incorporated herein by reference in their entirety for all purposes).

While the various foregoing systems and methods have proven some measure of effectiveness, the present invention provides for improvements over these systems and methods, in a number of respects.

BRIEF SUMMARY OF THE INVENTION

The present invention provides substrates, systems and methods for analyzing materials. In particular, in at least one aspect, the invention provides an analytical device that comprises a substrate comprising a first surface and at least a first optical waveguide disposed upon the first surface. The device includes an analyte disposed sufficiently proximal to the first surface and external to the waveguide, to be illuminated by an evanescent field emanating from the waveguide when light is passed through the waveguide, e.g., the light field that decays exponentially as a function of distance from the waveguide surface.

In another aspect, the invention provides a method of illuminating an analyte that comprises providing a substrate comprising a first surface and at least a first optical waveguide disposed upon the first surface. An analyte is provided disposed sufficiently proximal to the first surface and external to the waveguide, to be illuminated by an evanescent field emanating from the waveguide when light is passed through the waveguide. Light is then directed or propagated through the first waveguide such that the evanescent field from the waveguide illuminates the analyte.

In another aspect, the invention provides a system for analyzing an analyte that comprises a substrate comprising a first surface and at least a first optical waveguide disposed upon the first surface. At least a first light source is provided optically coupled to the at least first waveguide to direct light into the first waveguide. An optical detection system is also provided positioned to receive and detect optical signals from an analyte disposed sufficiently proximal to the first surface and external to the waveguide, to be illuminated by an evanescent field emanating from the waveguide when light is passed through the waveguide.

DETAILED DESCRIPTION OF THE INVENTION

I. General

Figure 1:
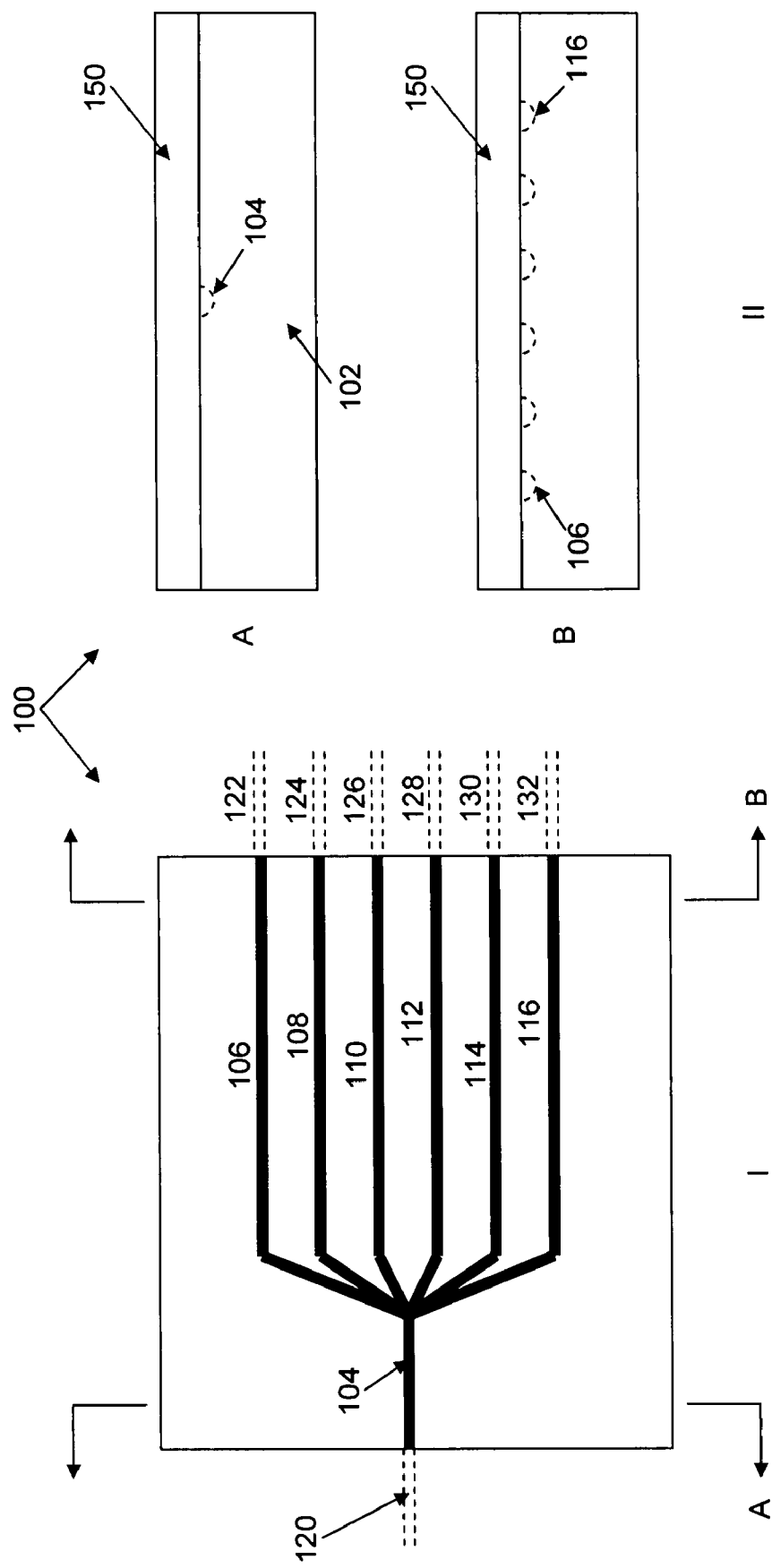
FIG. 1 schematically illustrates a Waveguide array used to split light from individual optical fibers into multiple optical fibers.

The present invention generally provides a simplified method for delivering illumination to a plurality of discrete analytical regions on a substrate, and does so in a manner that provides better control of that illumination. In particular, the present invention provides methods, systems and substrates that include surface exposed waveguides, such the exponential decay of light outside the waveguide may be exploited in the surface region in the same manner as the light that enters a ZMW, above, in order to selectively illuminate materials provided upon that surface.

The invention provides such substrates alone, as well as in conjunction with one or more other components in an overall system, such as reagents (e.g., dyes, enzymes, buffers and other adjuncts, and the like), illumination sources (e.g., lasers, lamps and the like), observation and detection components or systems (e.g., optical trains including lenses, mirrors, prisms, gratings and the like, detectors such as PMTs, Photodiodes, photodiode arrays, CCDs, EMCCDs, ICCDs, photographic films, and the like).

Also provided are methods and applications of the substrates and systems of the invention in the illumination and preferably the analysis of materials which more preferably include fluorescent or fluorogenic materials. As will be appreciated, the present invention is broadly applicable to any application in which one desires to illuminate materials that are at or proximal to a surface and/or specific locations on a surface, without illuminating materials that are not similarly situated. Examples of such analyses include illumination, observation and/or analysis of surface bound cells, proteins, nucleic acids or other molecules of interest.

In the context of analysis, the substrates, methods and systems of the invention impart numerous additional advantages to an analytical operation. In particular, because the light of interest is applied in a spatially focused manner, e.g., confined in at least one lateral and one orthogonal dimension, using efficient optical systems, e.g., fiber optics and waveguides, it provides a much more efficient use of illumination, e.g., laser, power. In addition, because illumination is provided from within confined regions of the substrate itself, issues of illumination of background or non-relevant regions, e.g., illumination of non-relevant materials in solutions, autofluorescence of substrates and/or other materials, reflection of illumination radiation, are substantially reduced. Likewise, this aspect of the invention provides an ability to perform many homogenous assays for which it would be generally applicable.

In addition to mitigating autofluorescence of the substrate materials, the systems described herein substantially mitigate auto-fluorescence associated with the optical train. In particular, in typical fluorescence spectroscopy, the excitation light is typically directed at the reaction of interest through at least a portion of the same optical train used to collect the fluorescence, e.g., the objective and other components. As such, autofluorescence of such components will contribute to the detected fluorescence level and provide a fair amount of noise in the overall detection. Because the systems direct excitation light into the substrate through a different path, e.g., through an optical fiber optically coupled to the waveguide in the substrate, this auto-fluorescence source is eliminated.

Other advantages include an automatic alignment of illumination with analytes of interest, as such alignment will be self defining, e.g., an analyte of interest may be that which is provided within a pre-existing illumination region. This level of alignment is also designed (and is thus programmable) and fabricated into the substrate and is thus not prone to any misalignment issues or other sensitivities of other analytical systems. As such, the alignment of illumination is highly robust.

Finally, the substrates of the invention typically are provided from rugged materials, e.g., glass, quartz or polymeric materials that have demonstrated longevity in harsh environments, e.g., extremes of cold, heat, chemical compositions, e.g., high salt, acidic or basic environments, vacuum and zero gravity. As such, they provide rugged capabilities for a wide range of applications.

Such illumination is particularly useful in illuminating fluorescent and/or fluorogenic materials upon or proximal to the surface, including nucleic acid array based methods, substrate coupled nucleic acid sequencing by synthesis methods, antibody/antigen interactions, and a variety of other applications. These and other applications are described below.

II. Substrates

In particularly preferred aspects, a waveguide substrate is used that provides for the propagation of a single beam and preferably its separation into multiple propagated beams in a waveguide array. Examples of such arrayed waveguides have been employed in the fiber optic based systems in splitting beams propagated by a single fiber into multiple fibers. Typically, however, such arrayed waveguides employ a cladding layer disposed over the waveguide carrying substrate. An example of such a device is schematically illustrated in FIG. 1. As shown in both a top view (Panel I) and side view (Panel II, A and B), the arrayed waveguide 100 includes a base substrate 102 that has a first refractive index. Portions of the substrate 104-116 are provided having a higher refractive index, thus allowing them to confine and propagate light introduced into them, functioning as waveguide cores. Typically, these arrayed waveguides receive light from a first optical fiber 120, that is optically coupled to the waveguides, e.g., connected such that light is transmitted from one to the other, and propagate (via waveguide 104) and optionally divide the light equally among the waveguides 106-116, which divided light is then propagated into optical fibers 122-132. As noted above, and with reference to panel II, both A and B views, the use of such devices in the fiber optic applications typically has necessitated the inclusion of a cladding layer 150, disposed over the surface of substrate 102, in order to better confine and/or isolate the light within the waveguides and to minimize propagation losses. While the substrates of the invention are preferably planar substrates having the waveguide(s) disposed therein, it will be appreciated that for certain applications, non-planar substrates may be employed, including for example, fiber based substrates, shaped substrates, and the like.

In contrast to the above described waveguide arrays, the present invention exploits the underlying waveguide substrate and waveguides, but eliminates the cladding layer that blocks access to the light that emanates from the waveguide, thus exposing the substrate surface and providing more proximal access to the evanescent light field emanating from the waveguides at the substrate surface. As noted previously, a large number of analytical operations can benefit from the ability to controllably illuminate materials at or near a surface and/or at a number of locations thereon, without excessively illuminating the surrounding environment. Further, although discussed in preferred aspects as providing access to the evanescent light from an array, it will be appreciated that modifications of waveguides to enhance direction of light propagating therethrough, toward the surface, are also contemplated by the invention, including, e.g., embedded gratings or other optical components embedded in the waveguide that direct light toward the surface region of interest on a substrate. Notwithstanding the foregoing, exploitation of the evanescent field is preferred as it gives rise to a desired limited illumination volume proximal to the surface of the substrate for a number of applications.

Figure 2:
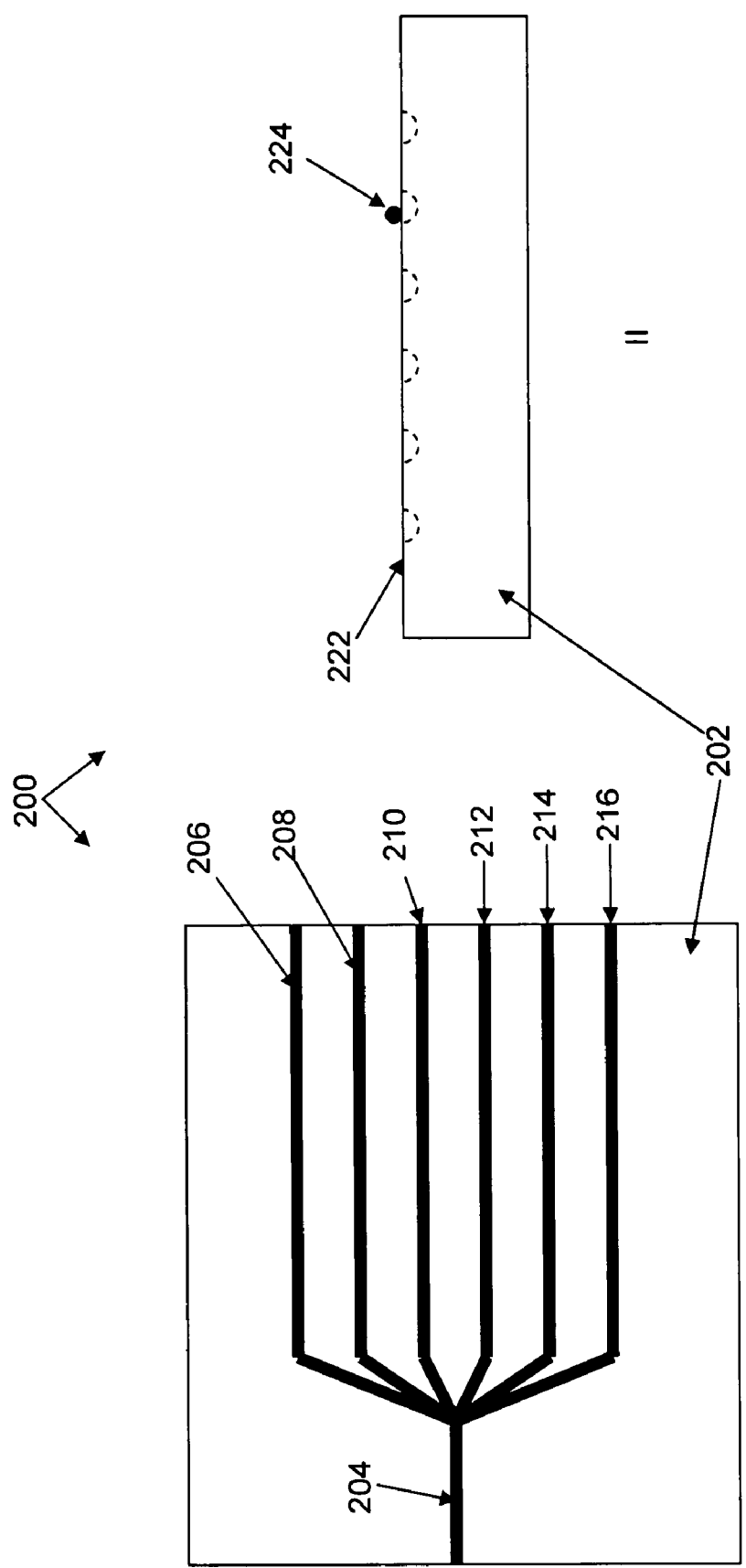
FIG. 2 schematically illustrates a substrate of the invention.

An example of the devices (also referred to herein as analytical devices) of the invention is schematically illustrated in FIG. 2. As with FIG. 1, the array 200 includes a substrate 202 in which are disposed an array of waveguides 206-216 optically coupled to an originating waveguide 204. For purposes of the present disclosure, an originating waveguide generally refers to a waveguide which is optically coupled to more than one additional waveguide, or in some cases, a waveguide that is provided in a substantially different configuration, e.g., a different substrate, a different spatial plane, or having a substantially different cross-section, refractive index, or path/shape configuration, or the like.

In the absence of a cladding layer, e.g., cladding layer 150 in FIG. 1, the waveguide cores are exposed at the surface 222 of the substrate, or are sufficiently proximal to that surface that the evanescent field emanating from the cores extends beyond the surface 222 of the substrate. For purposes of the invention, a waveguide that is referred to as being disposed upon or within the surface of a substrate encompasses waveguides that are disposed on but above the surface, within the substrate but at or exposed to the surface, or are disposed within the substrate, but sufficiently proximal to the surface that the evanescent wave from light passing through the waveguide still reaches above the surface to provide an illumination volume.

As noted previously, this provides access to the evanescent light outside of each waveguide core. By providing materials at or proximal to the surface, e.g., particle 224, one can controllably illuminate such materials without illuminating any materials outside of the evanescent field. Such selective illumination allows for illumination of individual or relatively small numbers of particles, molecules or cells in more concentrated solutions of such materials, as described in greater detail below. As will be appreciated, controllable illumination includes not only control of illumination in the axis orthogonal to the substrate or core surface (z axis), but also in at least one of the axes of the plane of the substrate surface (x or y axes). This lateral control of illumination, particularly when coupled with additional lateral control of analyte location, e.g., through the use of immobilization, or other spatial confinement techniques, e.g., structural barriers, etc., provides additional advantages of selectivity of observation.

Figure 3B:
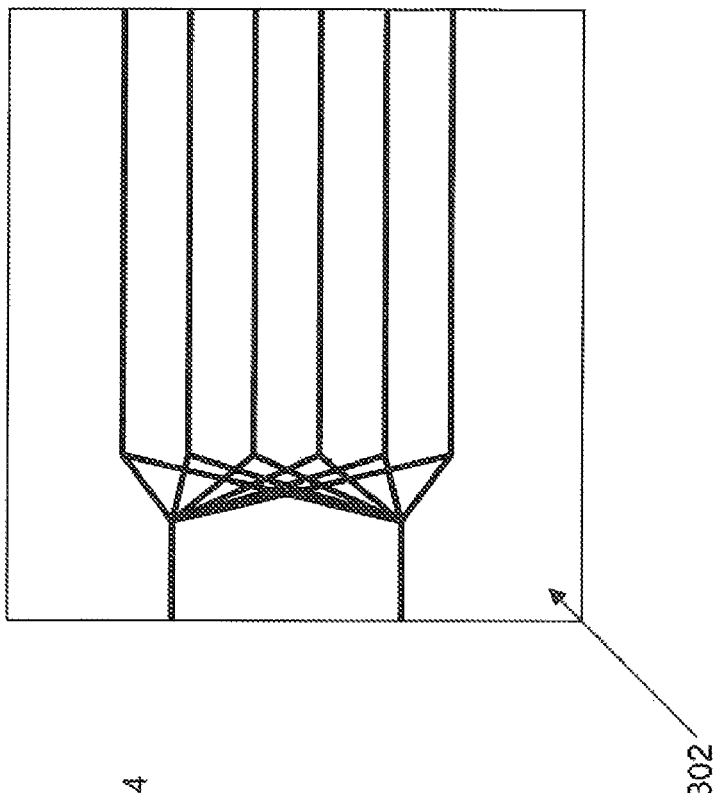
FIGS. 3A and 3B schematically illustrate alternate configurations of the substrates of the invention.
Figure 3A:
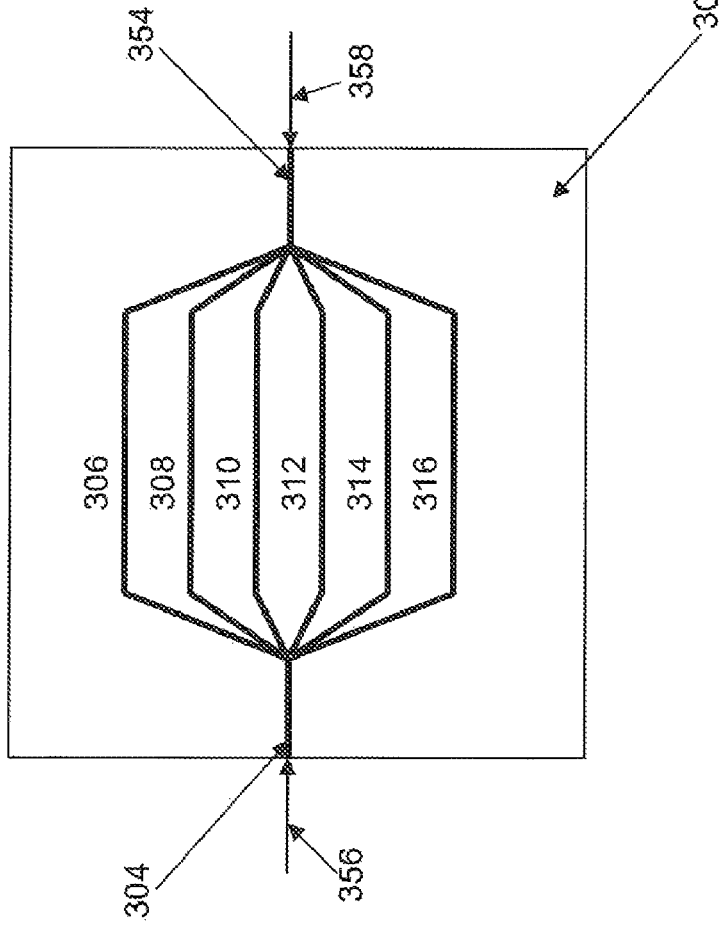

In accordance with the present invention, the substrates may include a variety of different configurations, depending upon the desired application(s). By way of example and as shown in FIG. 3A, a waveguide array 300 may include a substrate 302 having two or more originating waveguides 304 and 354 that are both in optical communication with the array of waveguides 306-316. Light sources having different characteristics, e.g., different spectral characteristics, frequencies, or the like, are directed into the separate originating waveguides (as shown by arrows 356 and 358), e.g., through a coupled optical fiber, in order to deliver illumination of different characteristics to the same set of waveguides 306-316, and consequently surface of the substrate. An alternative configuration is shown in FIG. 3B, where the two or more light sources provide light to two or more originating waveguides at the same end of the array substrate, and each originating waveguide is in optical communication with the same set or overlaps with at least a portion of the same set of waveguides in the array.

Alternatively, individual waveguide array substrates may include multiple originating waveguides, e.g., like originating waveguides 104 and 304 from FIGS. 1 and 3, respectively, that are each coupled to separate arrays of waveguides, in order to provide for higher multiplexing capabilities of each substrate, including performance of different analyses on a single substrate, e.g., using different light sources having differing characteristics.

The arrays may include parallel waveguides, e.g., as shown, or may include patterned waveguides that have a variety of different configurations, including serpentine waveguides, divergent waveguides, convergent waveguides or any of a variety of configurations depending upon the desired application. For example, where it is desired to provide evanescent illumination to larger areas of the substrate, it may be desirable to provide such serpentine waveguides, wider or slab waveguide(s), or alternatively and likely preferably, larger numbers of parallel or similarly situated waveguides. As noted previously, the waveguide substrates may include a single waveguide that may span a fraction of the width of the substrate or substantially all of that width. In accordance with preferred aspects however, waveguide arrays are used to split individual originating beams into two or more waveguides, preferably more than 10 waveguides, more than 20 waveguides, more than 40 waveguides, and in some cases more than 50 waveguides or even more than 100, 1000, 5000 or more waveguides. The number of waveguides may typically vary greatly depending upon the size of the substrate used, and the optical resolution of the detection system, e.g., its ability to distinguish materials proximal to different waveguides.

The waveguides may individually vary in the size of the core region in order to vary the evanescent field that one can access. Typically, the waveguides will have a cross sectional dimension of from about 0.1 to about 10 μm, preferably from about 0.2 to about 2 μm and more preferably from about 0.3 to about 0.6 μm. A variety of other waveguide dimensions may be employed as well, depending upon the desired application. For example, in some cases, a single waveguide may be used where the cross-sectional dimension of the waveguide is substantially the same as the substrate width or length, e.g., a single waveguide that substantially spans a substrate's width. Notwithstanding the foregoing, preferred aspects will provide arrayed waveguides, e.g., multiple waveguides typically arranged in parallel linear format.

Figure 4B:
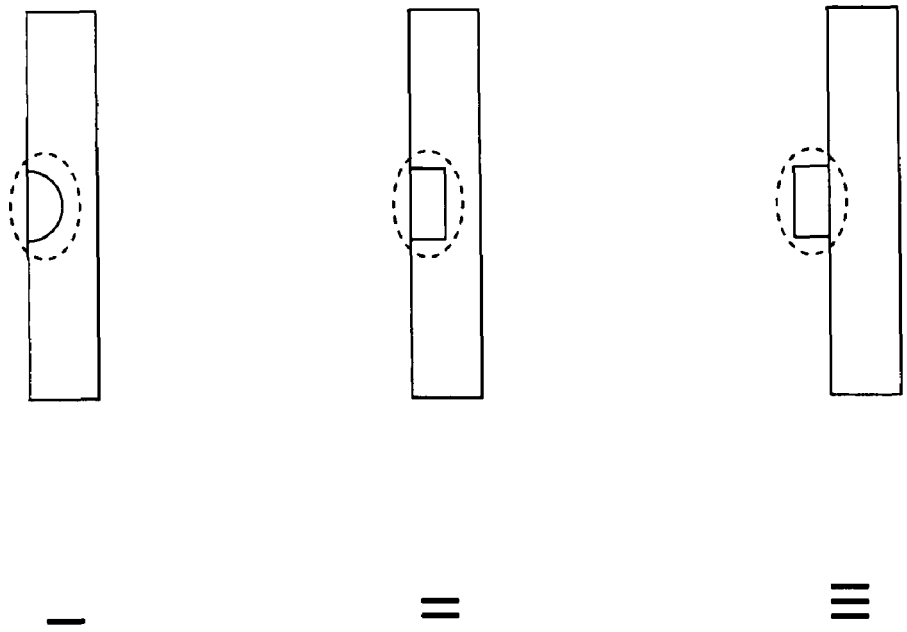
FIG. 4B schematically illustrates the shape of the evanescent electromagnetic field confined by each of the types of waveguides.
Figure 4A:
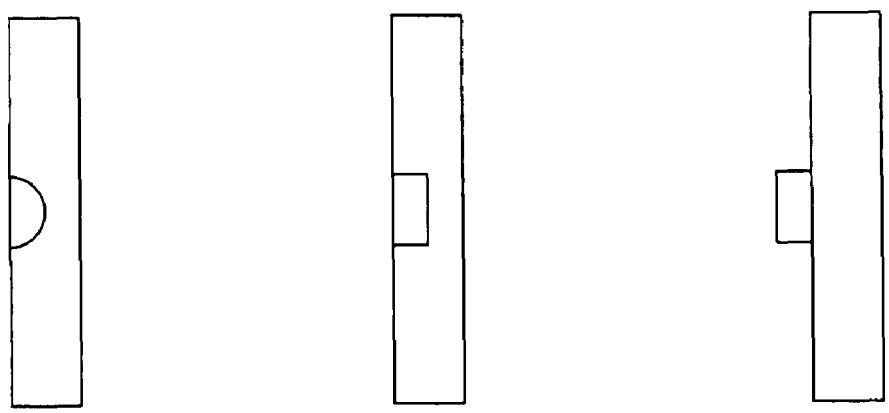
FIG. 4A schematically illustrates a number of waveguide types useful in the context of the invention.

Although described above in terms of a particular type of waveguide structure, e.g., an embedded waveguide structure, a variety of different waveguide structures are exploitable in the present invention, and are shown in FIG. 4A. In particular, the waveguide arrays of the invention may employ an embedded waveguide, e.g., as described above and shown in Panel I, and channel waveguides (Panel II and III). FIG. 4B provides a schematic illustration of the general shape of the evanescent field that would be yielded by each type of waveguide in FIG. 4A, Panels I-III, respectively (See, e.g., Saleh and Teich, Fundamentals of Photonics, (John Wiley and Sons, 1991) and particularly Chap. 7.2). For purposes of the present disclosure, the waveguides of the invention in which the core is exposed to or proximal to the substrate surface such that the evanescent field emanating form the core extends above the substrate surface, are generally referred to as being disposed upon the surface of the substrate, regardless of whether they extend the nominal surface of the substrate or are embedded therein, or even embedded thereunder, to some degree. Thus, for example, all of the waveguide configurations illustrated in FIGS. 4A and B are generally referred to as being disposed upon the surface of the substrate while for certain aspects, e.g., embedded waveguides, the core of the waveguide may additionally be referred to as being disposed within the surface of the substrate.

In some cases, the waveguides described herein are generally produced using conventional ion implantation techniques to selectively ion dope selected regions of $SiO_2$ substrates to provide patterned regions of higher refractive index, so as to function as waveguides embedded in the underlying substrate. Examples of such devices are disclosed in, e.g., Marcuse, Theory of Dielectric Optical Waveguides, Second Ed. (Academic Press 1991). Alternate waveguide fabrication processes and configurations are equally applicable to the present invention, including hybrid material waveguides, e.g., employing polymeric materials as a portion or all of the subject substrate, e.g., a polymer core having a first refractive index, disposed within a substrate of another material having a second refractive index, which may be polymeric, or another material, e.g., glass, quartz, etc.

Additional optical functionalities may be provided upon or within the substrates of the invention, including, e.g., providing additional optical confinements upon the substrate, such as zero mode waveguides as discussed in U.S. Pat. Nos. 6,991,726 and 7,013,054, previously incorporated herein by reference. Other optical functionalities that may be integrated into or upon the substrates including, e.g., mask layers, lenses, filters, gratings, antireflective coatings, or the like. Other functionalities may be incorporated into the fabricated substrate that operate on and/or in conjunction with the waveguides or waveguide arrays of the invention. For example, optical switching or attenuation components may be provided upon or within the substrates of the invention to selectively direct and/or modulate the light passing through a given waveguide or waveguides.

By way of example, the waveguide array may have a controllable optical switch or attenuator built into its structure which can provide control over the amount of light allowed to enter the waveguide structure. Such control permits the careful selection of optimal light levels for a given analysis being carried out using the substrate. Further, using independently activated switches or attenuators on a waveguide array permits one to independently control light application to one or a subset of waveguides in an array. In still other advantageous applications, in combination with multiple light sources coupled to the same waveguides through different originating waveguides, optical switching of the input waveguides will permit one the ability to select the light source(s) for any subset or all of the waveguides at a given time, or even to modulate the intensity of a light from a given source, on the fly. By controlling the light from individual sources, e.g., where such sources have differing spectra, one can consequently control the wavelength of the light reaching a given waveguide and its associated reaction regions.

In addition to the ability to more precisely control the light parameters of the overall system for precise tuning of the application, the controlled aspect of the light application provides further abilities to mitigate potential adverse effects of excessive illumination on reaction components, such as photo-damage effects on reactants, or other reaction components resulting from prolonged high intensity illumination.

A variety of different optical devices may be employed in controlling light passage through the waveguides used in the substrates of the invention. In particular, optical modulators, such as Mach-Zhender modulators (see, e.g., U.S. Pat. No. 7,075,695 for discussion of high speed Mach-Zhender modulators), Michelson modulators, thermally tunable modulators that may include other optical devices (see, e.g., Published U.S. Patent Application No. 2005-0232543 for a discussion of thermally tunable modulators) or may employ heating elements to modulate the refractive index of one or more waveguides, optical switches, and the like.

Figure 5:
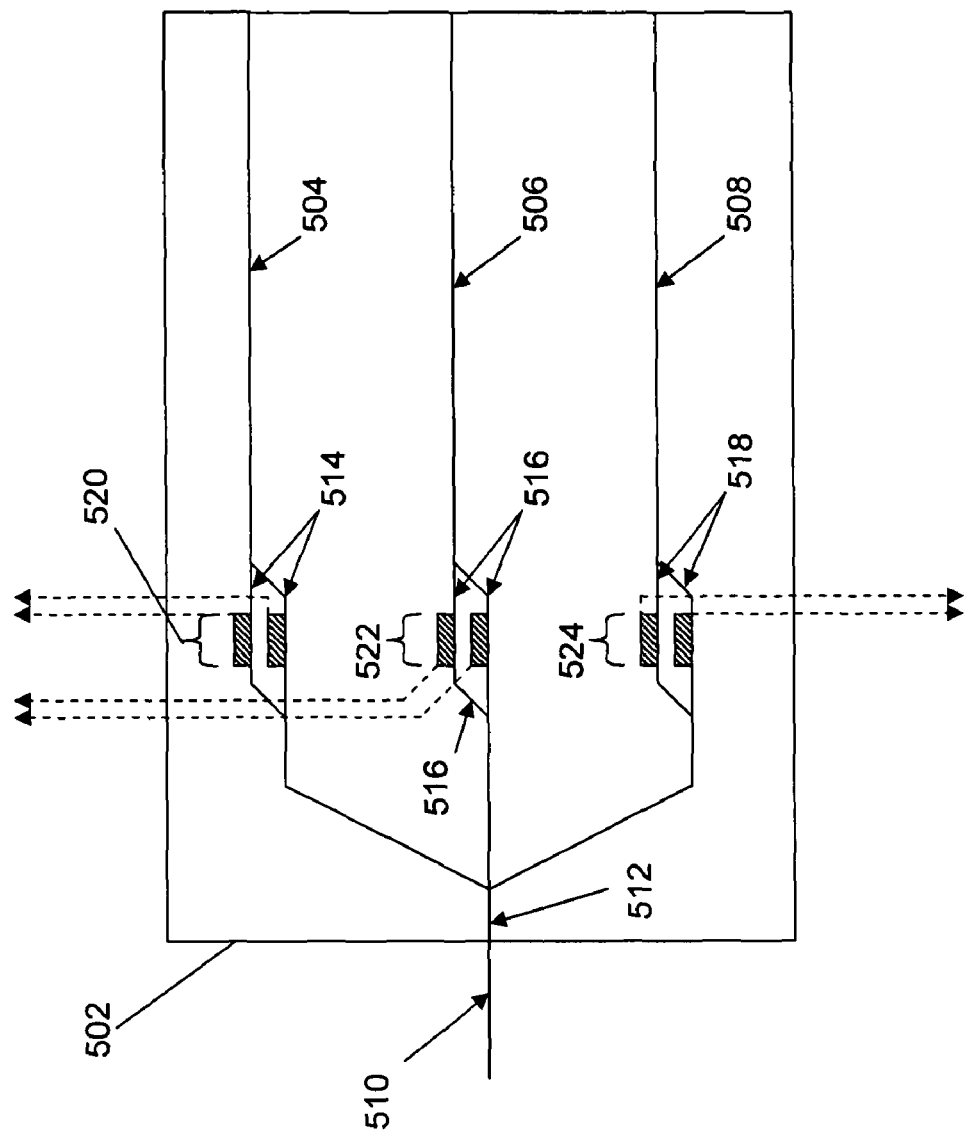
FIG. 5 schematically illustrates a substrate of the invention with integrated control elements.

FIG. 5 schematically illustrates the use of optical modulators in the context of the waveguide array based substrates of the invention. As shown, a substrate 502 is provided including a number of optical waveguides, e.g., surface exposed waveguides 504, 506 and 508. The waveguides 504-508 are optically coupled to a light source (not shown) via optical fiber 510 and input waveguide 512. Each of waveguides 504-508 includes a Mach-Zhender modulator, as shown by electrode pairs 520-524, respectively, and the associated branch waveguides (514-518, respectively). Although shown having dual electrode control, single electrode modulators may be employed (and in certain preferred aspects, are employed) to modulate the refractive index of one path to adjust the phase of light traveling therethrough. In particular, rather than electrode pair 520 being disposed over both channels of branch waveguide 514, only a single electrode would be disposed over one of the branch waveguides to modulate the phase of light passing therethrough. Similarly, in the context of interferometers employing thermal control rather than electric fields, it will be appreciated that a single heating element, e.g., taking the place of a single electrode, will typically be used. Preferred heating elements include resistive heaters disposed over the waveguide, e.g., patterned electrodes having high resistivity over the branch waveguide. Other heating elements may likewise be employed, including, e.g., infrared heating elements, peltier devices, and the like.

In addition to the optical functionalities of the substrates of the invention, in some cases, such substrates may include additional functionalities that provide a defined region on the substrate surface to limit the access that reagents or other elements have to the illumination zone above a waveguide. For example, in some cases, the substrates may include a patterned structure or set of structures over the surface of the substrate providing selected exposure of the surface exposed waveguide(s). Such selected regions may provide limited areas of illumination on a given substrate by blocking the illumination region existing above other portions of the waveguide(s). As a result, only selected portions of the surface will be within the illumination region of the waveguides. Such regions may be selected to align with detection systems or the requirements of such systems, e.g., sample spacing permitting spectral separation of signals from each region (See, e.g., U.S. patent application Ser. No. 11/704,733, filed Feb. 9, 2007, which is incorporated herein by reference in its entirety for all purposes). In addition to limited access, such structures may also provide structural confinement of reactions or their components, such as wells or channels. In one aspect, for example, microfluidic channels may be provided disposed over surface exposed waveguide or waveguide array. Such channels may be independently used to deliver different reagents to different portions of a waveguide or waveguide array.

Figure 6:
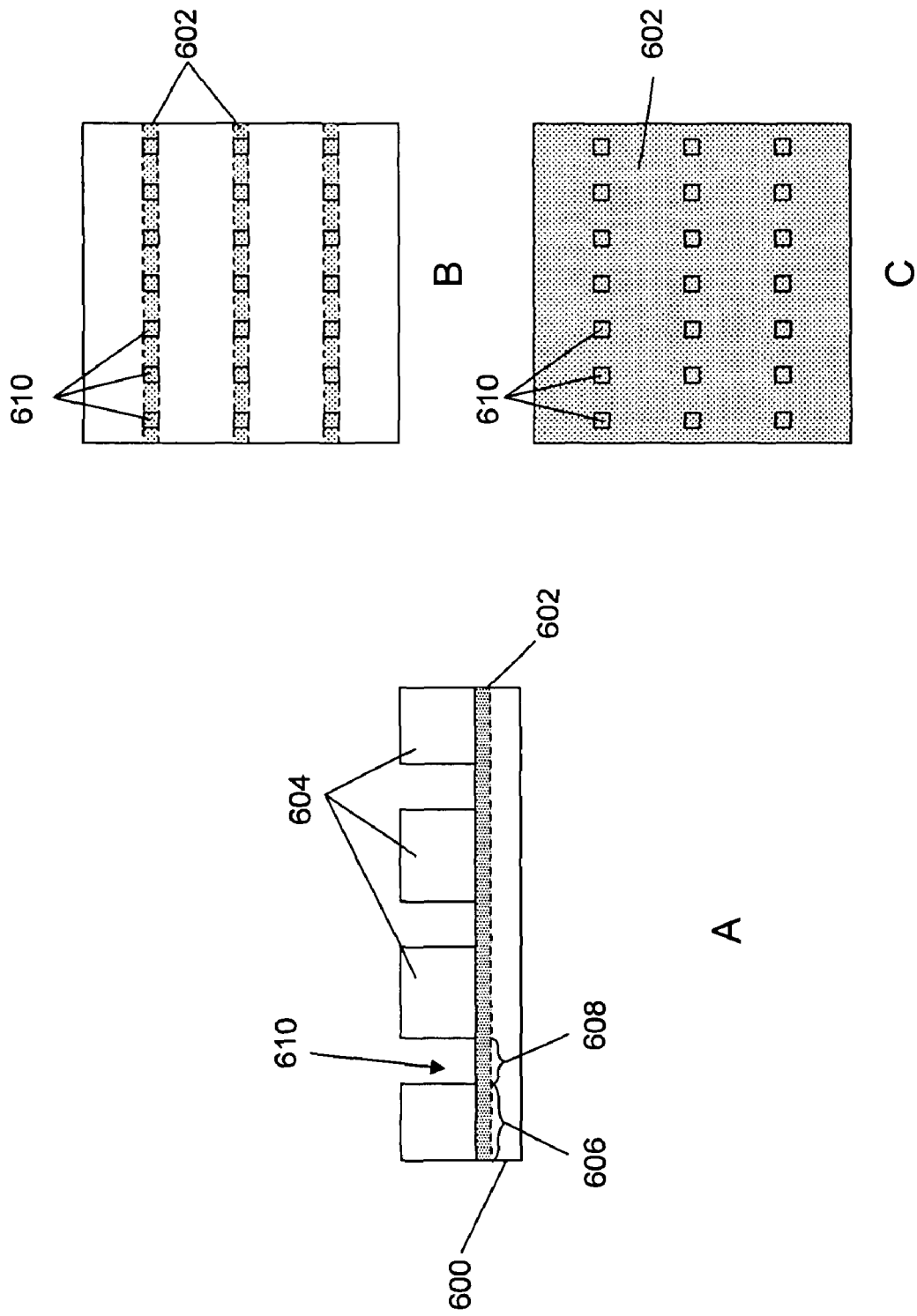
FIG. 6 schematically illustrates a waveguide substrate of the invention including a structural layer disposed over the waveguide surface.

FIG. 6 provides a schematic illustration of the structure of exemplary substrates according to this aspect of the invention. As shown in FIG. 6A, a first substrate 600 includes a waveguide 602 at or sufficiently proximal to the surface of the underlying substrate 600 that some of the evanescent wave from the waveguide 602 can reach above that surface. A mask layer 604 is provided over the underlying substrate that masks certain portions 606 of the waveguide but not other portions 608, that remain accessible to materials disposed over the overall substrate. In particular, the evanescent wave from exposed waveguide region 608 can reach reagents deposited over the surface of the overall substrate, and particularly within wells 610. By virtue of mask layer 604, the evanescent wave from the other blocked portions of the waveguide 606, will not reach any materials deposited over the surface of the substrate. As a result, one can pre-select those regions that are optically interrogatable, and thus direct optical systems appropriately. A top view of the overall substrate is shown in FIG. 6B, where the wells 610 are provided through the mask layer to expose portions of the underlying waveguides 602

Substrates including mask layer 604 may be prepared by a variety of known fabrication techniques. For example, lithographic techniques may be used to define the mask layer out of polymeric materials, such as photoresists, using e.g., conventional photolithography, e-beam lithography, or the like. Alternatively, lithographic techniques may be applied in conjunction with layer deposition methods to deposit metal mask layers, e.g., using aluminum, gold, platinum, chrome, or other conventionally used metals, or other inorganic mask layers, e.g., silica based substrates such as silicon, $SiO_2$, or the like. In particularly preferred aspects, both the underlying substrate and the mask layer are fabricated from the same material, which in particularly preferred aspects, is a transparent substrate material such as an $SiO_2$ based substrate such as glass, quartz, or fused silica. By providing the mask and underlying layers of the same material, one can ensure that the two layers have the same interactivity with the environments to which they are exposed, and thus minimize any hybrid surface interactions.

In the case of $SiO_2$ based substrates and mask layers, conventional fabrication processes may be employed. In particular, a glass substrate bearing the surface exposed waveguide has a layer of resist deposited over its surface. A negative of the mask layer is then defined by appropriate exposure and development of the resist layer to provide resist islands where one wishes to retain access to the underlying waveguide. The mask layer is then deposited over the surface and the remaining resist islands are removed, e.g., through a lift off process, to provide the openings to the underlying waveguides. In the case of metal layers, deposition may be accomplished through a number of means, including evaporation, sputtering or the like. Such processes are described in, e.g., U.S. Pat. No. 7,170,050, which is incorporated herein by reference in its entirety for all purposes. In the case of silica based mask layers, a CVD process may be employed to deposit a silicon layer onto the surface. Following lift off of the resist layer, a thermal oxidation process can convert the mask layer to $SiO_2$. Alternatively, etching methods may be used to etch access points to underlying waveguides using conventional processes. For example, a silicon layer may be deposited over an underlying waveguide substrate. A resist layer is then deposited over the surface of the silicon layer and exposed and developed to define the pattern of the mask. The access points are then etched from the silicon layer using an appropriate differential etch to remove silicon but not the underlying $SiO_2$ substrate. Once the mask layer is defined, the silicon layer is again converted to $SiO_2$ using, e.g., a thermal oxidation process.

In addition to the advantages of reduced auto-fluorescence, waveguide substrates having an integrated mask layer provide advantages of optical alignment over similar arrays of wells or structures. In particular, in illuminating an ordered array of reaction regions with minimal excess illumination, one typically presents a corresponding array of illumination spots. In doing so, one must take substantial care in aligning the optical presentation of the illumination spots to the ordered array of reaction regions. Such alignment presents challenges of both design and robustness, as such systems may be prone to drifting or other misalignment influences. Where, as in the present invention, illumination is hard wired into the substrate by virtue of the integrated waveguide, alignment is automatic.

In other cases, surface features may include other confinement strategies, including, e.g., chemical surface functionalities that are useful in a variety of surface analytical operations, such as hydrophobic coatings or hydrophilic coatings that are optionally patterned, to provide confinement or direction to aqueous materials, chemical derivatization, e.g., to facilitate coupling of other functional groups or otherwise, e.g., by providing hydrophobic barriers partially or completely surrounding a desired region. As will be appreciated, in some cases, particularly where structural confinement is provided upon the surface of the substrate, it may not be necessary to divide up light through a series of discrete waveguides in a given substrate. In particular, because one can obtain a desired level of multiplex and spatial separation organization from structurally dividing up the surface, one need not obtain that property through the use of separate waveguides. In such cases, a single field waveguide disposed at the surface of the substrate will suffice to deliver light to the various reaction regions on the surface of the substrate, e.g., as defined by the mask layer. An example of this is illustrated in FIG. 6C, where the waveguide 602 is shown (shaded) as extending across the entire surface area of the substrate 600 and the wells or apertures 610 through the mask layer, leave exposed portions of the waveguide 608 to define the access points to the evanescent wave coming from the waveguide.

In addition to structures and strategies that provide for positioning and/or confinement upon a substrate surface, other components may be provided upon a substrate, including backside coatings for the substrate, e.g., antireflective coatings, optical indicator components, e.g., structures, marks, etc. for the positioning and or alignment of the substrate, its constituent waveguides, and/or for alignment of other components. Other components may include substrate packaging components, e.g., that provide fluidic interfaces with the substrate surface, such as flow cells, wells or recesses, channel networks, or the like, as macrostructures as compared to the surface defined structures above, as well as alignment structures and casings that provide structural protection for the underlying substrates and interactive functionality between the substrates and instrument systems that work with/analyze the substrates.

III. Methods and Applications

A. Generally

As noted previously, the substrates, systems and methods of the invention are broadly applicable to a wide variety of analytical methods. In particular, the substrates of the invention may be employed in the illumination mediated analysis of a range of materials that are disposed upon or proximal to the substrate's surface. Such analyses include, inter alia, a number of highly valued chemical, biochemical and biological analyses, including nucleic acid analysis, protein interaction analysis, cellular biology analysis, and the like.

B. Exemplary Applications

1. Sequencing by Synthesis

One example of an analytical operation in which the present invention is particularly applicable is in the determination of nucleic acid sequence information using sequence by synthesis processes. Briefly, sequencing by synthesis exploits the template directed synthesis of nascent DNA strands, e.g., using polymerase mediated strand extension, and monitors the addition of individual bases to that nascent strand. By identifying each added base, one can deduce the complementary sequence that is the sequence of the template nucleic acid strand. A number of "sequence by synthesis" strategies have been described, including pyrosequencing methods that detect the evolution of pyrophosphate upon the incorporation of a given base into the nascent strand using a luminescent luciferase enzyme system as the indicating event. Because the indicator system is generic for all four bases, the process requires that the polymerase/template/primer complex be interrogated with only one base at a time.

Other reported sequence by synthesis methods employ uniquely labeled nucleotides or nucleotide analogs that provide both an indication of incorporation of a base, as well as indicate the identity of the base (See, e.g., U.S. Pat. No. 6,787,308). Briefly, these methods employ a similar template/primer/polymerase, complex, typically immobilized upon a solid support, such as a planar or other substrate, and interrogate it with nucleotides or nucleotide analogs that may include all four bases, but where each type of base bears an optically detectable label that is distinguishable from the other bases. These systems employ terminator bases, e.g., bases that, upon incorporation, prevent further strand extension by the polymerase. Once the complex is interrogated with a base or mixture of bases, the complex is washed to remove any non-incorporated bases. The washed extended complex is then analyzed using, e.g., four color fluorescent detection systems, to identify which base was incorporated in the process. Following additional processing to remove the terminating group, e.g., using photochemistry, and in many cases, the detectable label, the process is repeated to identify the next base in the sequence. In some cases, the immobilized complex is provided upon the surface as a group of substantially identical complexes, e.g., having the same primer and template sequence, such that the template mediated extension results in extension of a large number of identical molecules in a substantially identical fashion, on a step wise basis. In other strategies, complexes are immobilized in a way that allows observation of individual complexes resulting in a monitoring of the activity of individual polymerases against individual templates.

As will be appreciated, immobilization or deposition of the polymerase/template/primer complex upon or proximal to the surface of the waveguide core in the waveguide arrays of the invention will allow illumination, and more notably in the case of fluorescence based assays, excitation, at or near selected regions of the surface without excessive activation and fluorescence interference from the surrounding environment, which can be a source of significant noise in fluorescence based systems.

In another sequencing-by-synthesis process, one monitors the stepwise addition of differently labeled nucleotides as they are added to the nascent strand and without the use of terminator chemistries. Further, rather than through a one-base-at-a-time addition strategy, monitoring of the incorporation of bases is done in real time, e.g., without the need for any intervening wash steps, deprotection steps or separate de-labeling steps. Such processes typically rely upon optical strategies that illuminate and detect fluorescence from confined reaction volumes, such that individual complexes are observed without excessive interference from labeled bases in solution that are not being incorporated (See U.S. Pat. Nos. 6,991,726 and 7,013,054, previously incorporated herein, and 7,052,847, 7,033,764, 7,056,661, and 7,056,676, the full disclosures of which are incorporated herein by reference in its entirety for all purposes), or upon labeling strategies that provide fluorescent signals that are indicative of the actual incorporation event, using, e.g., FRET dye pair members on a base and on a polymerase or template/primer (See U.S. Pat. Nos. 7,052,847, 7,033,764, 7,056,661, and 7,056,676, supra).

Figure 7:
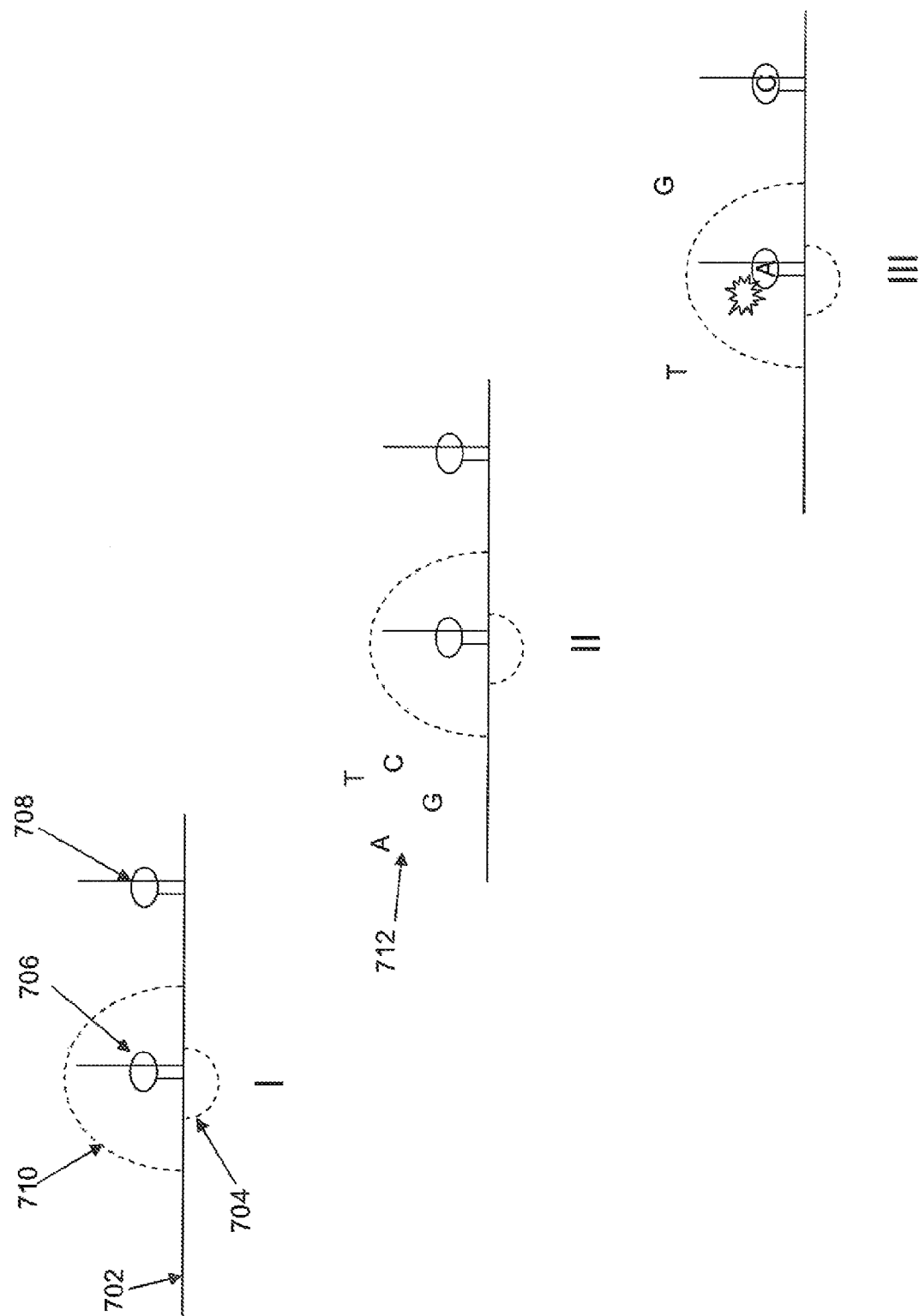
FIG. 7 schematically illustrates illumination of a molecular complex disposed upon a substrate of the invention.

This aspect of the invention is schematically illustrated in FIG. 7. As shown in panel I, a portion of a substrate surface 702 that includes a waveguide 704 as described herein, is provided with immobilized complexes 706 and 708 of the template nucleic acid sequence, a primer sequence and a polymerase enzyme. The illumination volume resulting from evanescent field emanating from the light propagating down the waveguide provides a relatively small volume in which fluorescent compounds will be excited, as shown by dashed field line 710. As a result, only those complexes sufficiently close to the waveguide core, e.g., complex 706, will be excited, and those outside this volume, e.g., complex 708, will not be illuminated. In the context of real time sequencing methods, the complex is interrogated with a mixture of all four, distinguishably labeled nucleotide analogs, e.g., nucleotides 712 (A, T, G, C) (see panel II). Upon incorporation (Panel III), a given nucleotide, e.g., A, will be retained within the illumination volume for a period longer than that which would occur based upon normal diffusion of bases into and out of the illumination volume, and as such is identifiable as an incorporated base. Bases in solution or not incorporated, e.g., T and G, or incorporated by non-illuminated complex, e.g., C, will not be illuminated and will therefore not be detected. By monitoring incorporation as it progresses, one can identify with reasonably high accuracy, the underlying template sequence. While a variety of methods may be employed, preferred methods of monitoring the reactions as they occur at the surface (or in the case of step-wise methods after they occur), is accomplished using detection systems as described elsewhere, herein. Although described in one exemplary application as being useful in real-time sequencing applications, it will be appreciated that the substrates methods and systems of the invention are equally applicable to the other sequence by synthesis applications described herein that employ illumination based activation of signaling or labeling mechanism, e.g., fluorescence based systems.

In accordance with the foregoing sequence by synthesis methods, one may optionally provide the complexes over an entire surface of a substrate, or one may selectively pattern the immobilized complexes upon or proximal to the waveguide cores. Patterning of complexes may be accomplished in a number of ways using selectively patternable chemical linking groups, and/or selective removal or ablation of complexes not in the desired regions. In some cases, one can employ the waveguides in selectively patterning such complexes using photoactivatable chemistries within the illumination region. Such strategies are described in detail in U.S. patent application Ser. No. 11/394,352 filed Mar. 30, 2006, and incorporated herein by reference in its entirety for all purposes.

In addition to selective immobilization, and as noted above, in some cases it is desirable to immobilize the complexes such that individual complexes may be optically resolvable, e.g., distinguished from other complexes. In such cases, the complexes may be immobilized using highly dilute solutions, e.g., having low concentrations of the portion of the complex that is to be immobilized, e.g., the template sequence, the polymerase or the primer. Alternatively, the surface activation for coupling of the complex component(s) may be carried out to provide a low density active surface to which the complex will be bound. Such surfaces have been described in U.S. patent application Ser. No. 11/240,662, filed Sep. 30, 2005, which is incorporated herein by reference in its entirety for all purposes. Again, such low density complexes may be patterned just upon or proximal to the waveguides or they may be provided across the surface of the substrate, as only those reaction complexes that are proximal to the waveguides will yield fluorescent signals.

While described in terms of real-time nucleic acid sequencing by synthesis, it will be appreciated that a wide variety of real-time, fluorescence based assays may be enhanced using the substrates, methods and systems of the invention.

2. Molecular Arrays and other Surface Associated Assays

Another exemplary application of the substrates and systems of the invention is in molecular array systems. Such array systems typically employ a number of immobilized binding agents that are each specific for a different binding partner. The different binding agents are immobilized in different known or readily determinable locations on a substrate. When a fluorescently labeled material is challenged against the array, the location to which the fluorescently labeled material binds is indicative of it's identity. This may be used in protein-protein interactions, e.g., antibody/antigen, receptor-ligand interactions, chemical interactions, or more commonly in nucleic acid hybridization interactions. See, U.S. Pat. Nos. 5,143,854, 5,405,783 and related patents, and GeneChip® systems from Affymetrix, Inc.

In accordance with the application of the invention to arrays, a number of binding regions, e.g., populated by known groups of nucleic acid probes, are provided upon a substrate surface upon or proximal to the waveguides such that a hybridized fluorescently labeled probe will fall within the illumination region of the waveguide. By providing for selective illumination at or near the surface, one can analyze hybridized probes without excessive interference from unbound fluorescent materials.

Figure 8:
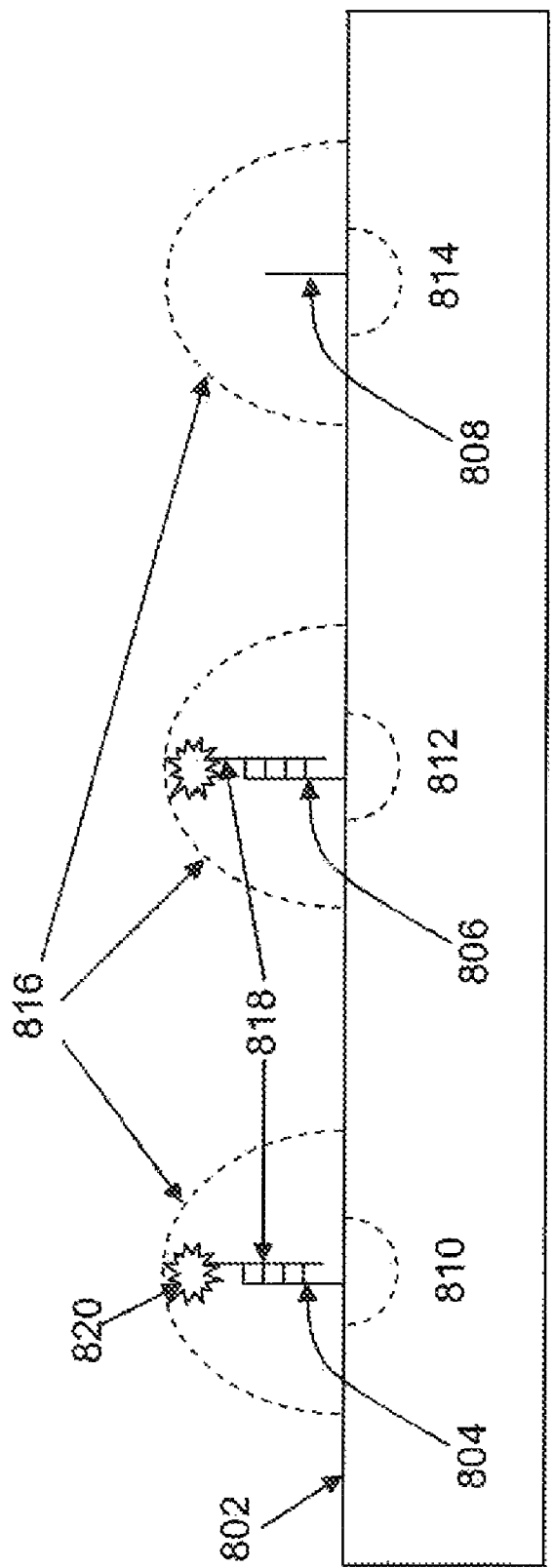
FIG. 8 schematically illustrates the use of the substrates of the invention in molecular array based systems.

This aspect of the invention is schematically illustrated in FIG. 8. As shown, a substrate surface 802 is provided with groups of molecules, e.g., nucleic acid probes 804, 806 and 808, where each probe group has a different binding specificity, e.g., to different complementary nucleic acid sequences. The groups are each provided upon or sufficiently proximal to a waveguide core, e.g., waveguide cores 810, 812, and 814, respectively, so that their respective illumination volumes, indicated by the dashed lines 816, encompasses a hybridized, fluorescently labeled probe 818. Illumination of the probe then excites the fluorescent label 820 allowing observation of hybridization. Such observation may be carried out post reaction, or in some cases as desired, in real time.

3. Cellular Observation and Analysis

In still another exemplary application, cell based assays or analyses may be carried out by providing cells adhered to the substrate surface over the waveguides. As a result, one could directly monitor fluorescently labeled biological functions, e.g., the uptake of fluorescent components, the generation of fluorescent products from fluorogenic substrates, the binding of fluorescent materials to cell components, e.g., surface or other membrane coupled receptors, or the like.

4. Other Applications

It will be appreciated by those of ordinary skill that the substrates of the invention may be broadly applicable in a wider variety of applications that analytical processes. For example, such substrates and methods may be employed in the identification of location of materials on surfaces, the interrogation of quality of a given process provided upon the surface, the photo-manipulation of surface bound materials, e.g., photo-activation, photo-conversion and/or photo-ablation. As such, while some of the most preferred applications of the present invention relate to analytical operations and particularly in the fields of chemistry, biochemistry, molecular biology and biology, the discussion of such applications in no way limits the broad applicability of the invention.

IV. Systems

In general, the substrates of the invention are employed in the context of other components as a system or one or more subsystems. By way of example, in preferred aspects, the substrates of the invention are employed in the analysis of materials disposed upon the substrate surface as described elsewhere herein. In such cases, the substrates of the invention are generally exploited in conjunction with and as a part of an analytical substrate and reagent system that is used in the desired analysis. Such reagent systems may include proteins, such as enzymes and antibodies, nucleic acids including nucleotides, nucleosides, oligonucleotides and larger polymers of same, substrates for a given reaction, cells, viruses or phages, or any of a variety of different chemical, biochemical or biological components for a desired analysis.

In addition to the "wet-ware" components of the systems set forth initially above, the invention also includes the substrates of the invention in conjunction with hardware and/or software system components. As noted previously, such hardware components include, e.g., optical components such as lenses, mirrors, prisms, illumination sources and the like, detection systems, while software components include processes for controlling overall systems and/or software for processing, evaluating and presenting data derived from those systems.

A. Reagent Systems and Kits

As set forth above, the substrates of the invention may be applied and/or packaged in kits with other reagents, buffers and other adjuncts that are used in the desired analysis. The nature of such reagents is generally application specific and will vary according to such applications. By way of example in application of such substrates to nucleic acid sequencing methods, as described below, the substrates may include one or more of template nucleic acids, nucleic acid probes, polymerase enzymes, native and/or normative nucleotides or nucleotide analogs, that will in certain preferred aspects, include labeling groups such as fluorescent labels. One or more of the foregoing components may be either packaged with and/or applied as immobilized components on the surface of the substrate that is exposed to the evanescent radiation from the waveguides.

In the context of application in real time sequencing by synthesis, reagent systems may include polymerase enzymes, e.g., as described in U.S. Patent Application No. 60/753,515 filed Dec. 22, 2005, which is incorporated herein by reference, or commercially available polymerase enzymes, e.g., taq polymerases, Sequanase® polymerases, Phi 29 polymerases, DNA Polymerase I, Klenow fragment, or any of a variety of other useful polymerases known to those of skill in the art. Additionally, such systems may include primer sequences that are either specific for a particular template sequence or are specific for a universal tag sequence that may be ligated to or otherwise provided in line with the template sequence. Such systems may further include nucleotides or nucleotide analogs, such as fluorescently labeled nucleotides like those described in U.S. patent application Ser. Nos. 11/241,809, filed Sep. 29, 2005, Published U.S. Application No. 2003/0124576, and U.S. Pat. No. 6,399,335, the full disclosures of which are all incorporated herein by reference for all purposes.

B. Optics and Instrumentation

As noted elsewhere herein, instrument systems are also included for use in conjunction with the substrates and methods of the invention. Typically, such systems include the substrates of the invention interfaced with appropriate light sources, such as one or more lasers, for delivering desired electromagnetic radiation through the waveguides. Also included is an appropriate optical train for collecting signals emanating from the substrate surface following illumination, and detection and data processing components for detecting, storing and presenting signal information.

Figure 9:
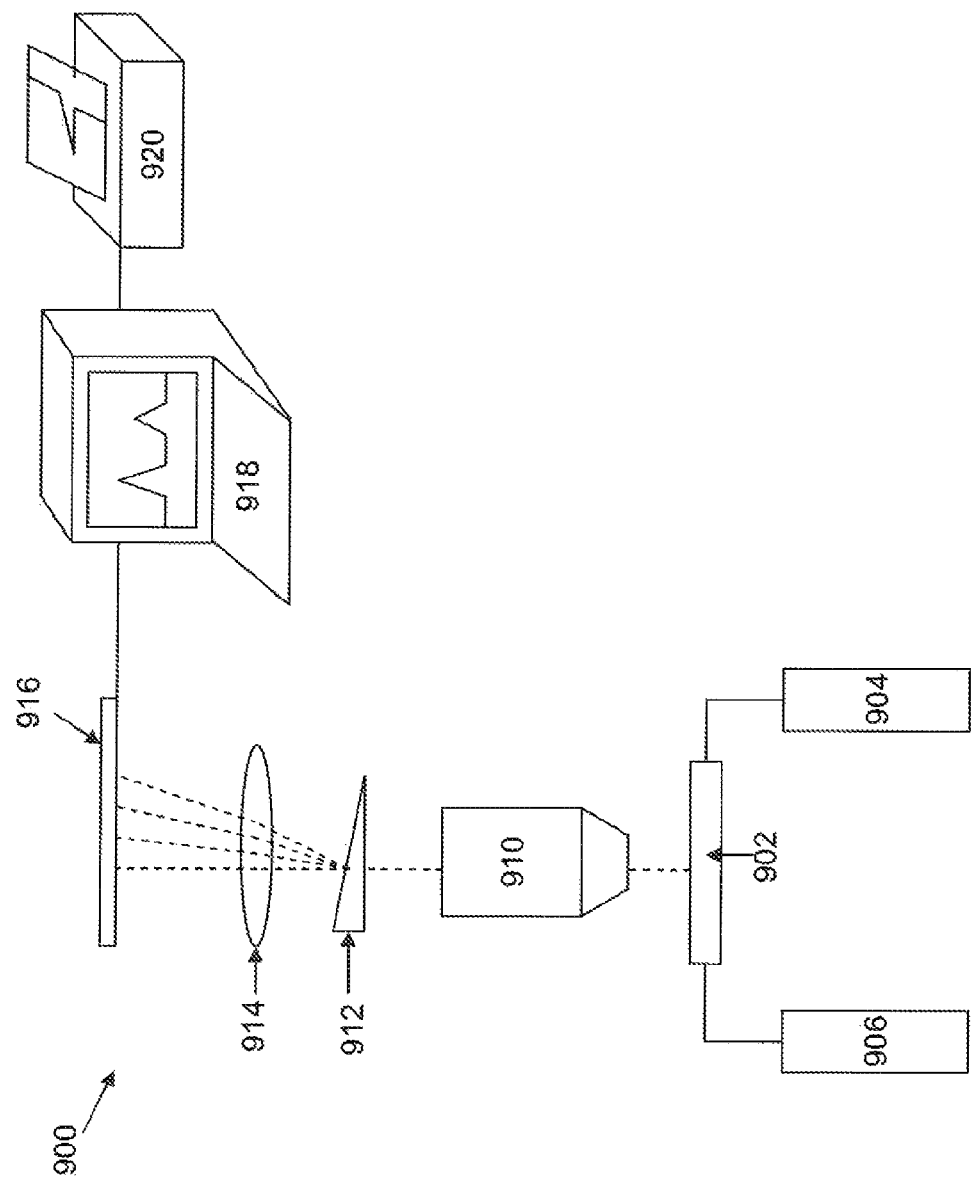
FIG. 9 schematically illustrates a system of the invention.

One example of a system for use in the present invention is illustrated in FIG. 9. As shown, the system 900 includes a substrate of the invention 902. Laser 904 and optional additional laser 906 are optically coupled to the waveguide array within the substrate, e.g., via optical fibers. An optical train is positioned to receive optical signals from the substrate and typically includes an objective 910, and a number of additional optical components used in the direction, filtering, focusing and separation of optical signals. As shown, the optical train includes a wedge prism for separating spectrally different signal components, and a focusing lens 914 that images the signal components upon an array detector, e.g., EMCCD 916. The detector is then operatively coupled to a data storage and processing system, such as computer 918 for processing and storage of the signal data and presentation of the data in a user desired format, e.g., on printer 920. As will be appreciated, a number of other components may be included in the systems described herein, including optical filters for filtering background illumination or bleed-through illumination from the light sources, from the actual optical signals. Additionally, alternate optical trains may employ cascaded spectral filters in separating different spectral signal components.

While illustrated with a first light source, e.g., laser 904, and an optional second light source, e.g., optional laser 906, it will be appreciated that additional light sources may be provided optically coupled to the waveguide arrays, e.g., using additional originating waveguides to direct light from each the various sources to all or a subset of the waveguides in a given array. For example, in some cases, 3 light sources, 4 light sources or more may be used. Additional light sources will preferably provide light having different spectral characteristics, e.g., peak wavelengths, to the waveguides, although they may also be employed to provide additional intensity or variations in other light characteristics, such as frequency.

The detection system is typically configured to detect signals from large areas of the substrate, e.g., multiple signals emanating from a plurality of different regions on the substrate, and preferably, do so simultaneously. Thus while scanning detection optics may be employed for certain applications of the invention, in general, larger area imaging detection systems are preferred.

Other optical trains and detection systems that may be employed in the present invention are described in U.S. patent application Ser. Nos. 11/201,768 (filed Aug. 11, 2005) and 60/772,908 (filed Feb. 13, 2006), each of which is incorporated herein by reference, which, with provision of a waveguide substrate of the invention and direction of excitation illumination through the waveguides, would be directly useful in the context of the invention. In particular, in certain aspects, the imaged signal will be a series of discrete signal sources or points of signal origin on the overall surface of the substrate. As such, the detection systems described in the aforementioned application would be directly applicable to the present invention.

Although described in some detail for purposes of illustration, it will be readily appreciated that a number of variations known or appreciated by those of skill in the art may be practiced within the scope of present invention. To the extent not already expressly incorporated herein, all published references and patent documents referred to in this disclosure are incorporated herein by reference in their entirety for all purposes.

What is claimed is:

1. A system for analyzing an analyte, comprising:
   a substrate comprising a first surface and at least a first optical waveguide disposed upon the first surface;
   at least a first light source optically coupled to the at least first waveguide to direct light into the first waveguide; and
   an optical detection system positioned to receive and detect an optical signal from an individual analyte disposed sufficiently proximal to the first surface and external to the waveguide to be illuminated by an evanescent field emanating from the waveguide when light from the light source is passed through the waveguide, wherein the individual analyte is immobilized on the first surface such that a signal from the individual analyte is optically resolvable from any other signal from any other analyte immobilized on the first surface and illuminated by the evanescent field.

2. The system of claim 1, wherein the optical detection system receives and detects signals from a plurality of locations on the surface of the substrate.

3. The system of claim 1, wherein the individual analyte comprises a fluorescent moiety that is excited by light of the wavelength provided by the first light source, and wherein the optical detection system comprises a detector for detecting fluorescent signals, and an optical train positioned to receive fluorescent signals from the first surface of the substrate and direct the fluorescent signals to the detector.

4. The system of claim 1, further comprising at least a second light source optically coupled to the at least first waveguide.

5. The system of claim 1, wherein the substrate comprises an optical switch or modulator disposed thereon for modulating light passing through the waveguide.

6. The system of claim 1, further comprising a mask layer disposed over a first portion of the waveguide, but not over a second portion of the waveguide.

7. The system of claim 6, wherein the second portion of the waveguide comprises at least a first well disposed through the mask layer.

8. The system of claim 6, wherein the second portion of the waveguide comprises a plurality of wells disposed through the mask layer.

9. The system of claim 6, wherein the mask layer is selected from a metal mask layer, a polymeric mask layer, and an inorganic mask layer.

10. The system of claim 9, wherein the mask layer comprises a photoresist layer.

11. The system of claim 9, wherein the mask layer is selected from aluminum, gold, platinum and chrome.

12. The system of claim 9, wherein the mask layer comprises a silica based mask layer.

13. The system of claim 1, wherein the substrate comprises a plurality of waveguides, and an originating waveguide disposed thereon, the originating waveguide being optically coupled to the at least first light source and each of the plurality of waveguides.

14. The system of claim 1, wherein the substrate has a refractive index that is lower than that of the first optical waveguide, and further wherein the first optical waveguide extends into and is at least partially enclosed by the substrate.

15. A system for analyzing an analyte, comprising:
- a substrate comprising a first surface and at least a first optical waveguide disposed upon the first surface, wherein the substrate comprises a plurality of optical waveguides disposed upon the first surface of the substrate, and further wherein the plurality of optical waveguides are spaced apart portions of the substrate having a higher refractive index than the substrate has between the plurality of optical waveguides;
- at least a first light source optically coupled to the at least first waveguide to direct light into the first waveguide; and
- an optical detection system positioned to receive and detect an optical signal from an individual analyte disposed sufficiently proximal to the first surface and external to the waveguide to be illuminated by an evanescent field emanating from the waveguide when light from the light source is passed through the waveguide, wherein the individual analyte is immobilized on the first surface such that a signal from the individual analyte is optically resolvable from any other signal from any other analyte immobilized on the first surface and illuminated by the evanescent field.

16. The system of claim 15, wherein the substrate comprises at least 10 waveguides disposed upon the first surface.

17. The system of claim 16, wherein the substrate comprises a plurality of optical switches or modulators to control light passing through each of the at least 10 waveguides.

18. The system of claim 15, wherein the substrate comprises at least 20 waveguides disposed upon the first surface.

19. The system of claim 15, wherein the substrate comprises at least 40 waveguides disposed upon the first surface.

* * * * *